United States Patent
Hays et al.

(10) Patent No.: US 12,207,954 B2
(45) Date of Patent: *Jan. 28, 2025

(54) MEDICAL VOICE COMMAND INTEGRATION

(71) Applicant: CERNER INNOVATION, INC., Kansas City, MO (US)

(72) Inventors: Chad Hays, Overland Park, KS (US); Randy Lantz, Parkville, MO (US)

(73) Assignee: CERNER INNOVATION, INC., Kansas City, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 18/314,496

(22) Filed: May 9, 2023

(65) Prior Publication Data

US 2023/0270390 A1 Aug. 31, 2023

Related U.S. Application Data

(63) Continuation of application No. 17/165,683, filed on Feb. 2, 2021, now Pat. No. 11,690,578, which is a (Continued)

(51) Int. Cl.
*G10L 15/22* (2006.01)
*A61B 5/00* (2006.01)
(Continued)

(52) U.S. Cl.
CPC .......... *A61B 5/749* (2013.01); *A61B 5/0022* (2013.01); *A61M 5/142* (2013.01);
(Continued)

(58) Field of Classification Search
CPC .......... G10L 17/22; G10L 15/22; G16H 40/00
See application file for complete search history.

(56) References Cited

U.S. PATENT DOCUMENTS 6,081,782 A * 6/2000 Rabin .................... G10L 17/22
704/251
9,842,591 B2 * 12/2017 George .................. G16H 20/17
(Continued)

OTHER PUBLICATIONS

U.S. Appl. No. 16/051,123, Non-Final Office Action, Mailed On Jan. 30, 2020, 8 pages.
(Continued)

*Primary Examiner* — Daniel Abebe
(74) *Attorney, Agent, or Firm* — MUGHAL GAUDRY & FRANKLIN PC

(57) ABSTRACT

System and methods for controlling healthcare devices and systems using voice commands are presented. In some aspects a listening device may receive voice command from a person. The voice command may be translated into human readable or machine readable text via a speech-to-text service. A control component may receive the text and send device-specific instructions to a medical device associated with a patient based on the translated voice command. In response to the instructions, the medical device may take an action on a patient. Some examples of actions taken may include setting an alarm limit on a monitor actively monitoring a patient and adjusting the amount of medication delivered by an infusion pump. Because these devices may be controlled using a voice command, in some cases, no physical or manual interaction is needed with the device. As such, multiple devices may be hands-free controlled from any location.

20 Claims, 7 Drawing Sheets

Related U.S. Application Data continuation of application No. 16/051,123, filed on Jul. 31, 2018, now Pat. No. 10,925,551.

(60) Provisional application No. 62/541,514, filed on Aug. 4, 2017.

(51) Int. Cl.

| | | |
|---|---|---|
| *A61M 5/142* | (2006.01) | |
| *A61M 16/00* | (2006.01) | |
| *G06F 3/16* | (2006.01) | |
| *G16H 40/63* | (2018.01) | |
| *G16H 40/67* | (2018.01) | |
| *A61B 5/318* | (2021.01) | |
| *A61B 17/00* | (2006.01) | |
| *G16H 10/60* | (2018.01) | |
| *G16H 50/20* | (2018.01) | |

(52) U.S. Cl.
CPC ........... *A61M 16/022* (2017.08); *G06F 3/167* (2013.01); *G10L 15/22* (2013.01); *G16H 40/63* (2018.01); *G16H 40/67* (2018.01); *A61B 5/0006* (2013.01); *A61B 5/318* (2021.01); *A61B 5/6898* (2013.01); *A61B 5/746* (2013.01); *A61B 2017/00017* (2013.01); *A61B 2017/00119* (2013.01); *A61B 2017/00203* (2013.01); *A61M 2205/3375* (2013.01); *A61M 2205/3553* (2013.01); *A61M 2205/3561* (2013.01); *A61M 2205/3584* (2013.01); *A61M 2205/3592* (2013.01); *A61M 2205/502* (2013.01); *A61M 2205/52* (2013.01); *A61M 2205/60* (2013.01); *A61M 2205/609* (2013.01); *A61M 2205/80* (2013.01); *G10L 2015/223* (2013.01); *G16H 10/60* (2018.01); *G16H 50/20* (2018.01)

(56) References Cited

U.S. PATENT DOCUMENTS

| | | | |
|---|---|---|---|
| 10,441,696 B2* | 10/2019 | Tanenbaum | G10L 17/22 |
| 2001/0032085 A1 | 10/2001 | Goedeke et al. | |
| 2005/0101250 A1 | 5/2005 | Helal et al. | |
| 2005/0108057 A1* | 5/2005 | Cohen | G16H 40/20 |
| | | | 705/3 |
| 2008/0081956 A1 | 4/2008 | Shah et al. | |
| 2012/0296181 A1 | 11/2012 | Islam | |
| 2013/0030807 A1 | 1/2013 | Burns et al. | |
| 2013/0138444 A1* | 5/2013 | George | G16H 20/60 |
| | | | 704/275 |
| 2015/0151050 A1 | 6/2015 | Estes | |
| 2018/0211656 A1 | 7/2018 | Chong et al. | |
| 2018/0311004 A1 | 11/2018 | Cagle et al. | |
| 2019/0038236 A1 | 2/2019 | Hays et al. | |
| 2019/0180603 A1 | 6/2019 | Kinney et al. | |

OTHER PUBLICATIONS

U.S. Appl. No. 16/051,123, Final Office Action, Mailed On Jun. 23, 2020, 10 pages.

U.S. Appl. No. 16/051,123, Notice of Allowance, Mailed On Oct. 23, 2020, 8 pages.

U.S. Appl. No. 17/165,683, Non-Final Office Action, Mailed On Nov. 1, 2022, 5 pages.

U.S. Appl. No. 17/165,683, Notice of Allowance, Mailed On Feb. 13, 2023, 7 pages.

\* cited by examiner

```
                    MedicalDeviceVoiceCommandIntentHandler.txt
// MedicalDeviceVoiceCommandIntentHandler.swift
import Intents // This class defines the logic for handling medical device voice commands for
setting alarm threshold limits.
// For example a user could say "Set John Smith's high heart rate limit to 95."
class MedicalDeviceVoiceCommandIntentHandler: INExtension,
INSendMessageIntentHandling, URLSessionDelegate {

// Handle the intent after it has been processed by the speech-to-text service.
        func handle(sendMessage intent: INSendMessageIntent, completion:
@escaping
(INSendMessageIntentResponse) -> Void) {
                let message = intent.content; // the raw speech-to-text
                let scanner = Scanner.init(string: message!);
                scanner.scanUpToCharacters(from: CharacterSet.decimalDigits, into:
nil); // find the numeric value to set // Test for key phrases such as "heart rate low", "heart rate high", etc.
                if(message?.lowercased().contains("heart"))! {
                        if(message?.lowercased().contains("low"))! {
                                var lowerLimit = Int();
                                scanner.scanInt(&lowerLimit);
                                sendCommand(parameter: "HEART_RATE_LOW_LIMIT",
limit: lowerLimit);

}
                        else if(message?.lowercased().contains("high"))! {
                                var upperLimit = Int();
                                scanner.scanInt(&upperLimit);
                                sendCommand(parameter: "HEART_RATE_HIGH_LIMIT",
limit: upperLimit);
                        }
                }
                else if (message?.lowercased().contains("spo2"))! {
                        if(message?.lowercased().contains("low"))! {
                                var lowerLimit = Int();
                                scanner.scanInt(&lowerLimit);
                                sendCommand(parameter: "SPO2_LOW_LIMIT", limit:
lowerLimit);
                                        .
                                        .
                                        .

CONTINUES IN FIG. 5B
```

*FIG. 5A.*

CONTINUES FROM FIG. 5A

.
.
.

```
            }
            else if(message?.lowercased().contains("high"))! {
                    var upperLimit = Int();
                    scanner.scanInt(&upperLimit);
                    sendCommand(parameter: "SPO2_HIGH_LIMIT", limit: upperLimit);
            }
        }
        else if (message?.lowercased().contains("respiratory"))! {
            if(message?.lowercased().contains("low"))! {
                    var lowerLimit = Int();
                    scanner.scanInt(&lowerLimit);
                    sendCommand(parameter: "RESPIRATORY_RATE_LOW_LIMIT", limit:.
                                MedicalDeviceVoiceCommandIntentHandler.txt
lowerLimit);
            }
            else if(message?.lowercased().contains("high"))! {
                    var upperLimit = Int();
                    scanner.scanInt(&upperLimit);
                    sendCommand(parameter: "RESPIRATORY_RATE_HIGH_LIMIT", limit: upperLimit);
            }
        }
    } let userActivity = NSUserActivity(activityType: NSStringFromClass(INSendMessageIntent.self));
        let response = INSendMessageIntentResponse(code: .success, userActivity: userActivity);
        completion(response);
    }

// Sends the command to the medical device
    func sendCommand(parameter: NSString, limit: Int) -> Void {
        let deviceID = "someDeviceId";
        let host = "someHost";
            .
            .
            .
```

CONTINUES IN FIG. 5C

*FIG. 5B.*

CONTINUES FROM FIG. 5B

...

```
// Build the request
var request = URLRequest(url: URL(string: "http://" + host + "/sendCommand/" + deviceID)!);
request.httpMethod = "POST";
request.addValue("application/json", forHTTPHeaderField: "Content-Type");

// Fill out the parameters
let json = NSMutableDictionary();
json.setValue(parameter, forKey: "parameter");
json.setValue(limit, forKey: "limit");

do {
        // Create the request body
        let data = try JSONSerialization.data(withJSONObject: json, options: JSONSerialization.WritingOptions.prettyPrinted);
        request.httpBody = data;

// Send the command to the device
        let session = URLSession.init(configuration: URLSessionConfiguration.default, delegate: self, delegateQueue: nil);
        let task = session.dataTask(with: request) { data, response, error in
                guard let data = data, error == nil else {
                        print("error= \(String(describing: error))");
                        return;
                }

MedicalDeviceVoiceCommandIntentHandler.txt
                // Print the response
                let response = String(data: data, encoding: .utf8);
                print("response = \(String(describing: response))");
        }
        task.resume();
}
catch {
        print("error= \(error)");
    }
  }
}
```

*FIG. 5C.*

MEDICAL VOICE COMMAND INTEGRATION

CROSS-REFERENCES TO RELATED APPLICATIONS

This application is a continuation of, and claims priority from, U.S. patent application Ser. No. 17/165,683, filed Feb. 2, 2021, which is a continuation of U.S. patent application Ser. No. 16/051,123, filed Jul. 31, 2018, now U.S. Pat. No. 10,925,551, issued Feb. 23, 2021, which claims the benefit of U.S. Provisional Application No. 62/541,514, filed Aug. 4, 2017, all of which are hereby expressly incorporated by reference in their entireties for all purposes.

BACKGROUND

In the traditional healthcare system, patients interact with numerous types of healthcare equipment, many of which are computer controlled in some fashion. For example, patients may interact with ventilators; dialysis equipment; or many variations of monitors, such as blood pressure monitors, heart rate monitors, or electrocardiograph (ECG) monitors. In another sense, patients may interact with equipment over which the patients have control. For example, these may include a device for summoning assistance, a patient controlled analgesia (PCA) pump, or mobility equipment. In many instances, caregivers must give a medical order for patients to use various types of equipment. For example, a clinician in a hospital may allow a patient to self-administer pain medication intravenously as needed up to a certain threshold using a PCA. However, these various types of healthcare systems and equipment are just a few that can be found in the traditional healthcare facility.

A problem arises in healthcare facilities as the number and variation of computer controlled devices increases. One such problem is that these devices require manually setting the equipment to perform the requested functions. Healthcare staff members and caregivers are required to undergo training for each of these systems. In most cases, a medical order by a clinician may be relayed through several hospital staff members before the appropriately trained staff member adjusts the necessary equipment in accordance with the order. As a result of this, there is a significant amount of inefficiency and a constant probability of error.

Another problem that these computer controlled medical devices create is that they require a person to manually adjust the device, such as manually setting alarm limits on a monitoring device actively monitoring a patient. In many scenarios, manually adjusting the healthcare equipment is very difficult or impossible at a particular time. One such example may be found in a quarantine unit. In quarantine units, clinicians and hospital staff may have to engage in various protocols for entering the patient room. This is timely and expensive, and may cause unnecessary risk to the patient because of the delay. In another example, a surgeon currently operating on a patient may wish to adjust or alter a computer controlled medical device associated with the patient. However, due to the risk of infection and operating room protocols, the surgeon may not be able to physically adjust the medical device. Again, it may require that the surgery be paused, require the surgeon to wait, or may require another staff member just for this request.

Further, many of these systems are not integrated with each other and are not integrated with the patient's medical records. There is no interoperability among these systems and patient records. Thus, in some cases, these systems may function independently and, in some cases, to the detriment of a patient. An example of this may occur if a staff member mistakenly inputs an incorrect threshold into a computer controlled device, such as a PCA pump. The wrong dosage or wrong pharmaceutical may be input into the system. Because the PCA pump does not have the ability to communicate with the patient's medical records, there is no mechanism to double check the received inputs and determine that the system has been set to a limit outside the threshold specified in the order.

SUMMARY

The present technology generally relates to devices, systems, and methods for using voice commands to control medical devices and systems. In some cases, the medical devices may be integrated with patient medical records.

In brief, and at a high level, the present disclosure describes technology that may receive a voice command from a user. In some instances, the voice command may be verified or validated. The voice command may be translated into a set of instructions. These instructions may be delivered to any number of computer controlled medical devices associated with a patient. In response, the device may take an action associated with the patient in accordance with the instructions.

As such, many of the problems associated with conventional technologies may be solved using this technology. For instance, in some aspects, a central listening device may receive voice commands from a verified individual (such as a clinician). An example command may be to change a threshold value on a monitoring device or generate a medical order. The device may translate the voice command into a set of usable instructions that may be delivered to any number of devices. Thus, in some scenarios, a clinician may be able to adjust monitoring equipment without manually or physically having to adjust the device. At the same time, the clinician may use a voice command to, for example, increase the dosage of a medication being administered to the patient through a computer controlled medication dispenser associated with the patient. And before leaving the patient, using only a voice command or a series of voice commands, the clinician may generate a medical order to be stored in the patient's medical records.

Because each of these devices and monitors is controlled via a voice command, it may no longer be necessary to have a specially trained individual adjust the device. This reduces the chance that error may occur when an order is relayed through multiple people. Further advantages may arise where it is difficult or impossible to adjust equipment or record an order in a medical record, such as in a quarantine unit or in an operating room. In these scenarios, the appropriate caregivers may be able to make necessary adjustments to the equipment without breaking the required protocol.

One aspect of the present technology that may accomplish these objectives is a system for controlling medical devices. In this aspect, the system comprises a microphone configured to receive voice commands from a user; a medical device associated with a patient; a processor in communication with the microphone and the medical device associated with the patient; and one or more computer-readable media storing computer-readable instructions. When the instructions are executed by the processor, they cause the processor to receive a voice command that has instructions for the medical device associated with the patient, translate the instructions for use by the medical device, and send the translated instructions to the medical device. In response to the instructions, the medical device takes an action in accordance with the translated instructions.

In another aspect of the present technology, a system for controlling medical devices is provided. The system comprises a listening component that is configured to detect a voice command from a user; a translation component that is configured to translate the voice command into a set of instructions; a control component configured to receive the set of instructions and communicate the set of instructions to one or more medical devices, causing the one or more medical devices to take an action in accordance with the set of instructions.

In yet another aspect of the present technology, a method for controlling medical devices is presented. The method comprises receiving, at a listening device, a voice command from a user; translating the voice command into a set of instructions; receiving, at a control component, the set of instructions; and sending, via the control component, a device-specific command based on the set of instructions to a medical device associated with the patient. In response, the medical device takes an action in accordance with the set of instructions.

Additional objects, advantages, and novel features of the technology are described below in the Detailed Description. They will, in part, become apparent to those skilled in the art, or they may be learned by practice of the technology.

BRIEF DESCRIPTION OF THE DRAWINGS

The present technology is described in the Detailed Description with reference to the attached figures, wherein:

FIGS. 5A-5C present a computer-readable code for implementing an exemplary use scenario in accordance with an aspect described herein.

DETAILED DESCRIPTION

The subject matter of the present technology is described with specificity to meet statutory requirements. However, the description itself is not intended to limit the scope of this disclosure. Rather, the inventors have contemplated that the claimed subject matter might also be embodied in other ways, to include different steps or combinations of steps similar to the ones described in this document, in conjunction with other present or future technologies. Moreover, although the terms "step" may be used herein to connote different elements of methods employed, the term should not be interpreted as implying any particular order among or between various steps disclosed, unless the order of individual steps is explicitly described.

Embodiments of the present technology are directed to methods, systems, and computer-readable media for integrating healthcare devices and systems with voice command. Certain aspects may provide for using voice commands to control medical devices and systems. In some aspects, the voice command technology may be integrated with an electronic medical record system. One example of the present technology is a device comprising a listening component, such as a microphone, that is configured to receive a voice command from a user, such as a clinician. The device may also comprise a processor that is in communication with medial equipment associated with a patient. In some cases, the processor may be communicatively coupled to an electronic healthcare system. The device may further comprise computer-readable media storing instructions that may be executed by the processor to receive, at the microphone, a voice command, translate the voice command into instructions for the medical equipment, and communicate the instructions to the medical equipment so that the medical equipment may take an action on a patient in accordance with the instructions. By integrating a listening component with a medical device and/or system, the medical device and/or system is improved because a user may interact with the device and/or system remotely. This remote operation further improves methods and processes of treating a patient because it does not require an operator to be in physical proximity to tactilely interact with the system and/or device. This reduces delay in the administration of a medication, for example, improving the efficiency and efficacy of treatment. Further aspects and embodiments are described in detail below.

Figure 1:
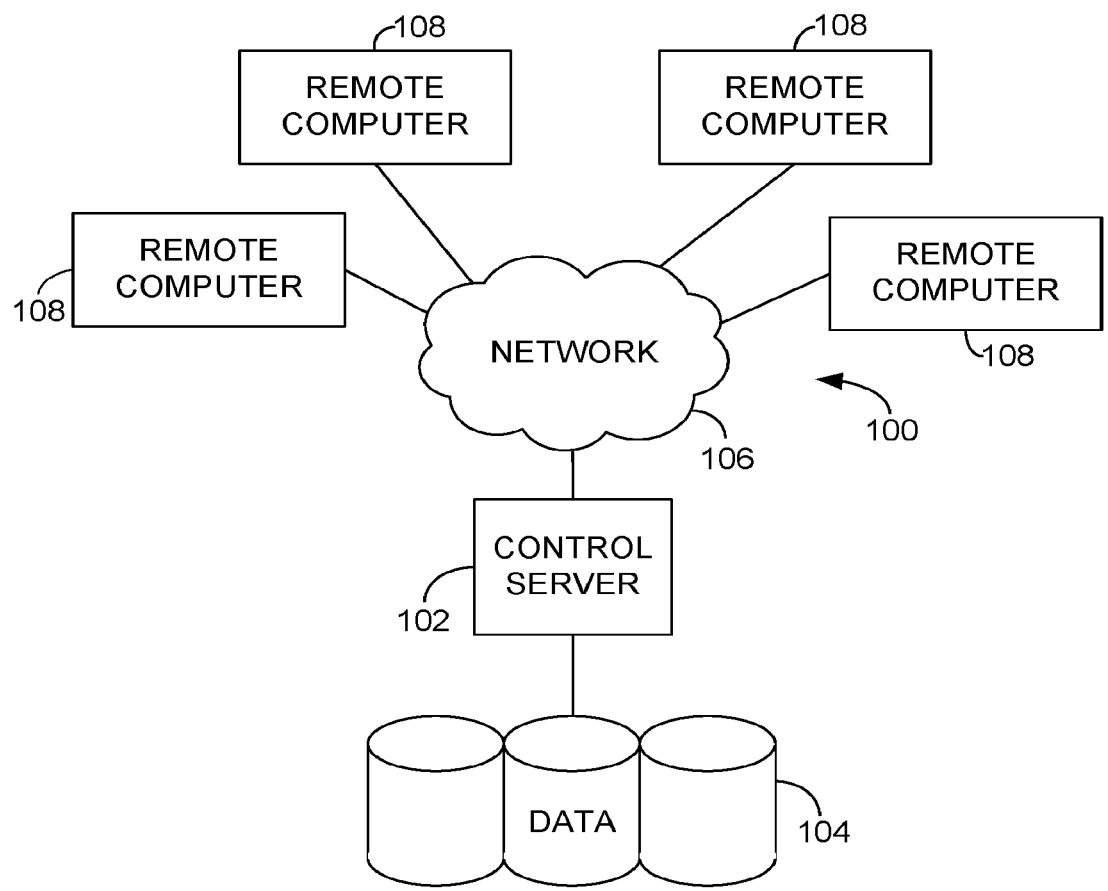
FIG. 1 is a block diagram of an exemplary computing environment suitable to implement aspects of the technology in accordance with an aspect herein.

With reference now to FIG. 1, an exemplary computing environment suitable for use in implementing aspects of the technology is described below. An exemplary computing environment (e.g., medical-information computing-system environment) with which embodiments may be implemented is provided. The computing environment is merely an example of one suitable computing environment and is not intended to suggest any limitation as to the scope of use or functionality of the technology. Neither should the computing environment be interpreted as having any dependency or requirement relating to any single component or combination of components illustrated therein.

The present technology might be operational with numerous other purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, stationary personal assistants, distributed computing environments that include any of the above-mentioned systems or devices, and the like.

The present technology might be described in the general context of computer-executable instructions, such as program modules, being executed by a computer. Exemplary program modules comprise routines, programs, objects, components, and data structures that perform particular tasks or implement particular abstract data types. The present technology might be practiced in distributed computing environments where tasks are performed by remote processing devices that are linked through a communications network. In a distributed computing environment, program modules might be located in association with local and/or remote computer storage media (e.g., memory storage devices).

The computing environment comprises a computing device in the form of a control server 102. Exemplary components of the control server comprise a processing unit, internal system memory, and a suitable system bus for coupling various system components, including data stores, with the control server. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes, or has access to, a variety of non-transitory computer-readable media. Computer-readable media can be any available media that might be accessed by control server, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server. Computer-readable media does not include signals per se.

Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network using logical connections to one or more remote computers 108. Remote computers 108 might be located at a variety of locations including operating systems, device drivers and medical information workflows. The remote computers might also be physically located in traditional and nontraditional medical care environments so that the entire healthcare community might be capable of integration on the network. The remote computers might be personal computers, servers, routers, network PCs, peer devices, other common network nodes, or the like and might comprise some or all of the elements described above in relation to the control server. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server, the data store 104, or any of the remote computers. For example, various application programs may reside on the memory associated with any one or more of the remote computers 108. It will be appreciated by those of ordinary skill in the art that the network connections shown are exemplary and other means of establishing a communications link between the computers (e.g., control server and remote computers) might be utilized.

In operation, an organization might enter commands and information into the control server or convey the commands and information to the control server via one or more of the remote computers through input devices, such as a keyboard, a microphone (e.g., voice inputs), a touch screen, a pointing device (commonly referred to as a mouse), a trackball, or a touch pad. Other input devices comprise satellite dishes, scanners, or the like. Commands and information might also be sent directly from a remote healthcare device to the control server. In addition to a monitor, the control server and/or remote computers might comprise other peripheral output devices, such as speakers and a printer.

Although many other internal components of the control server and the remote computers are not shown, such components and their interconnection are well known. Accordingly, additional details concerning the internal construction of the control server and the remote computers are not further disclosed herein.

Figure 2:
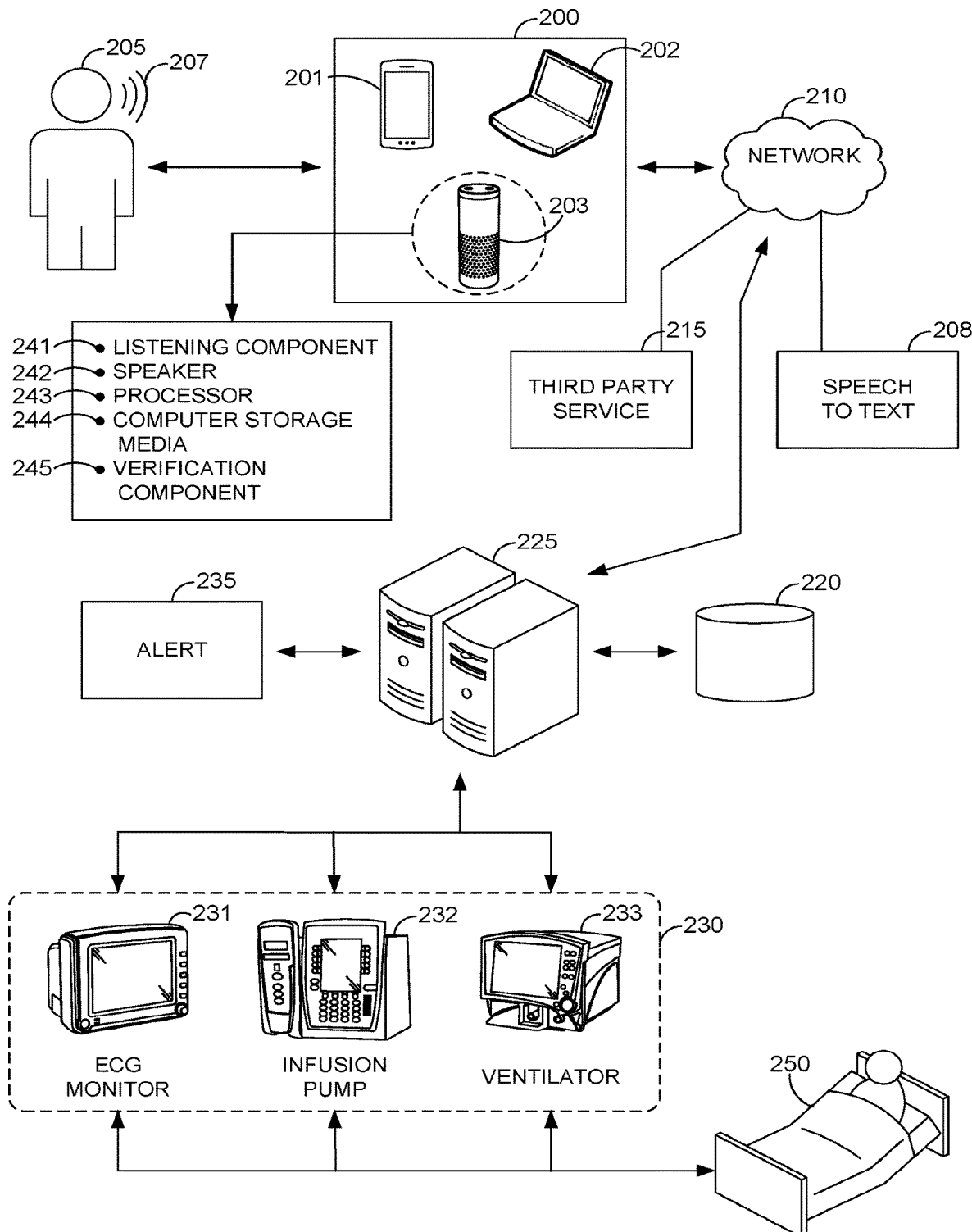
FIG. 2. is an block diagram of an exemplary integrated voice command system in accordance with an aspects herein.

Turning now to FIG. 2, FIG. 2 illustrates a block diagram of an exemplary integrated voice command system. In this particular aspect, the system comprises a listening device 200, a speech-to-text component 208, a network 210, a datastore 220, a command component 225, and a medical device 230. Although many of these components are described as individual components or functional entities, in some cases, they may be implemented as discrete or distributed components, or in conjunction with other components, having any suitable location or combination.

The system, as illustrated, comprises a listening device 200. The listening device 200 may include devices such as a mobile phone 201, a notebook computer 202, or a stationary personal assistant 203. The listening device 200 may include other types of mobile devices or wearables, such as a smart watch, a tablet, and the like. The listening device 200 may have a listening component 241 for detecting an audible signal 207, for example a voice command from a user 205. One common example of a type of listening component 241 is a microphone. In some aspects, the listening component 241 may also be a separate component that is communicatively coupled, for example, by hardwire or wireless, to other components of the system, further described herein. In one example the listening component 241 may be integrated into any equipment or integrated into the physical structure of a room within a facility.

The audible signal 207 may be detected from a user 205. In general, any person could be considered a user of this system. Some non-limiting examples may include a clinician, a patient, a hospital staff member, a nurse, an at-home caretaker, and the like. The audible signal 207 may be a voice command, such as a command for a device to perform some action or a command to generate a medical order for a patient 250. In some cases, the audible signal 207 may be in the form of a question. The system is not limited to a single user, but it may comprise many users at the same time.

The listening device 200 may further comprise a speaker 242, a processor 243, and computer storage media 244. The speaker 242 may be used to provide feedback to the user 205. For example, the speaker 242 may provide feedback that a particular command has been performed, or for confirmation to perform a command. In some aspects, the speaker 242 may be used to prompt the user 205 for more information or convey to the user 205 that the command is invalid. Other components, such as the processor 243 and the computer storage media 244 may be similar to those described with respect to the exemplary computing environment of FIG. 1.

The listening device 200 may be communicatively coupled to a network 210. Network 210 may include, without limitation, one or more local area networks (LANs) and/or wide area networks (WANs). In exemplary implementations, network 210 comprises the Internet and/or a cellular network, amongst any of a variety of possible public and/or private networks. In some aspects, the network 210 may be a cloud computing network. The network 210 may be in communication with a speech-to-text component 208. In some cases the speech-to-text component 208 may be a service in communication with network 210. For example, the speech-to-text component 208 may convert the audible signal 207 into readable text. In some cases, the audible signal 207 may be a voice command. The speech-to-text component 208 may translate the voice command into readable text, such as a set of instructions to control a medical device 230. The readable text may be human readable or machine readable. In some cases, the network 210 may communicate with a third-party service 215 to receive information. For example, information received from the third-party service 215 may be environmental information that may affect the health of some patients based on diagnosed ailments. In some aspects, the network 210 may receive information from the third-party service 215 through a computer application, or more generally, the Internet.

The listening device 200 may further comprise or be communicatively coupled to a verification component 245. The verification component 245 may verify the identity of a particular user. The particular user's identity may be verified, for example, by location, by device, by voice, and/or by authorization code. For example, the user's 205 location may be tracked throughout a facility. When the user 205 is within a certain proximity to the listening device 200, the user 205 may be verified when making a request or command. In another scenario, the user 205 may be verified by device. The listening device 205 may be in the form of a wearable associated with a particular user or may be a mobile device carried by the particular user. The use of the associated wearable or mobile device may identify the particular user. In some cases, the user 205 may be identified by voice. For instance, a particular user has a distinct voice signature that may be pre-associated with the particular user in, for example, datastore 220. When the listening device 200 detects the distinct voice signature, the verification component 245 may associate the voice signature with the particular user, thereby, verifying the particular user. In another case, verification may be performed using an authorization code, such as a password or PIN number. The code may be predetermined and stored in association with a particular user. When the listening device detects the code, the verification component may associate the code with the particular user to verify the user.

In some cases, verification of a particular user may be done to authorize the request. For example, in a hospital setting, clinician authorization may be required for the patient 250 to increase or begin taking a controlled substance. To keep non-clinicians, including the patient 250, from ordering the controlled substance via voice command, verification of the user 205 may be performed to authorize the request. Thus, in some cases, if the user 205 is making a request, and the user's 205 identity cannot be verified, the request may be denied. In other cases, the identity of the user 205 may be verified, but the user 205 may not have the proper pre-associated status to authorize the request. For example, if a nurse were to attempt to order a medication for the patient that has not been previously authorized by a clinician, the request may be denied pending the clinician's approval. In some aspects, a notification may be sent to the appropriate individual, such as the clinician, to authorize or deny the request. However, in some cases, if the user 205 is verified and authorized, the action may be taken to fulfill or comply with the request.

The listening device 200 may further be integrated with or communicatively coupled to a control component 225. The control component 225 may be in communication with a datastore 220. The datastore 220 may be an electronic health information system that stores medical records of patients. The control component 225 may further be in communication with one or more of the medical devices 230. In some cases, the control component 225 may send alerts or notifications. In some cases, the control component 225 may be synonymous with the verification component 245. Put another way, there may be no distinction between these components, as the control component 225 may perform the functions of verifying and authorizing the user 205.

In some aspects, the control component 225 may receive the translated audible signal 207, such as a set of instructions, from the speech-to-text component 208 or the listening component 200. In some aspects, the control component 225 may receive the translation and send a device-specific command to the medical devices 230 based on the translation. In some cases, prior to sending the device-specific command, the control component 225 may authorize the user 250 based on the user's verified identity. In some instances, the control component 225 may request verification prior to sending the device-specific command to ensure that the appropriate request or instructions are followed.

The medical devices 230 (or medical equipment) that are in communication with the control component 225 may be any number of computer controlled or assisted medical devices. Some non-limiting examples include an ECG monitor 231, an infusion pump 232, and a ventilator 233. In some aspects, these devices may be associated with the patient 250. For example, the ECG may be actively monitoring the patient 250, the infusion pump 232 may be delivering intravenous medication to the patient 250, while the ventilator 233 may be controlling the patient's 250 breathing.

In some aspects, each of the medical devices 230 may be controlled via the control component 225. For example, the control component 225 may send computer readable instructions to the ECG monitor 231 to increase or decrease for an alarm threshold for a measured unit, such as pulse rate. Thus, for example, an action taken on patient 250, in some cases, may be setting an alarm threshold for a monitor associated with the patient. Thus, in some instances, there may not be a physical action to patient 250, but there may be an adjustment to one or more of the medical devices 230 or equipment monitoring the patient 250. Similarly, the control component 225 may send computer-readable instructions to infusion pump 232 to alter a medication, for example, to increase, decrease, begin, or end medication delivered to the patient. Likewise, the control component 225 may send computer readable instructions to the ventilator to adjust an alarm limit or to adjust the patient's 250 breathing rate. In each of these scenario's, the control component 225 sends instructions in a manner that may be understood or interpreted by the medical device 230 so that the medical device 230 may take an action on the patient 250. There are many more computer controlled/assisted medical devices that may be found or used in the healthcare setting, each with one or more actions that may be performed on a patient. Both current and future computer assisted or controlled medical devices may be communicatively coupled to the control component 225.

In some cases, the control component 225 serves to integrate each of the medical devices 230 with the electronic health records system. This integration allows the medical devices 230 to be adjusted in accordance with the patient's 250 medical records. For example, the patient 250 may have a standing order from a clinician stored in the medical records. Later, a caretaker, after evaluating the patient 250, may wish to alter one of the medical devices 230 associated with the patient 250. Using a voice command, the caregiver may request that the medical device 230 be altered. The control component 225, based on the medical records of the patient 250, may alter the medical device 230 in accordance with the instructions if the instructions match the order stored in the medical records. However, for example, if the instructions did not match those stored in the medical records, such as a pain medication request that is above a threshold amount, the control component 225 may reject the request. In some cases, the control component 225 may send a request or a notification to the appropriate individual to get permission to fulfill the request.

In some cases, feedback may be provided to user 205, such as the caregiver after making a request. In some cases, the feedback may confirm that the request has been completed or is being processed; the feedback may also be a prompt by the system for the user 205 to provide clarification or more information, or to provide a different request; and the like.

In some scenarios, integration with the medical record system may allow medical devices 230 to store information about the patient 250 in the electronic medical record system. For example, a medical device 230 that is monitoring the patient 250 may store information, such as heart rate, blood pressure, oxygen statistics, and so on. In some cases, the control component 225 may store information collected by medical devices 230 based on a set of rules or criteria, such as if patient information contains a critical value, or if it deviates from a baseline value. The control component 225 may send notifications or alerts to the appropriate individuals based on the monitored information.

The control component 225 may further integrate the patient's 250 electronic medical records with the third-party service 215. Notifications and/or recommendations may be sent to the patient 250 based on information received from the third-party service 215 when compared to the patient's 250 medical records. For example, the patient may have severe allergies to pollen. From a third-party service 215 the control component 225 may receive information that, on a given day, the pollen count will be elevated. The control component 225, based on the patient 250 having pollen allergies, may send a notification to the patient 250 that has a recommendation to increase a preventative medication or to carry a rescue inhaler. Similar alerts and notification may be provided based on a standing medical order in the electronic medical record system.

Because the medical devices 230 may be controlled via a central control component 225, in some instances, this may eliminate the need to physically interact with the medical devices 230. For example, a user 205 may make an audible request that is received by the listening device 200 and translated by the speech-to-text component 208. Once received by the control component 225, the control component 225 may send instructions in accordance with the request to the proper medical device 230 so that the medical device will make the adjustment in accordance with the request. Thus, in some instances, an authorized person will be able to make adjustments over a range of various medical devices 230 without having to be trained on how to manually operate each individual device. Additionally, the person requesting may not even need to be in the same room. For example, the request could be audibly made from outside of a quarantine room. The control component 225 would then adjust the appropriate medical device 230 within the room in accordance with the request. Thus, not only does the person making the request not have to interact manually with the devices, but they may also interact with the devices from a distance.

Figure 3:
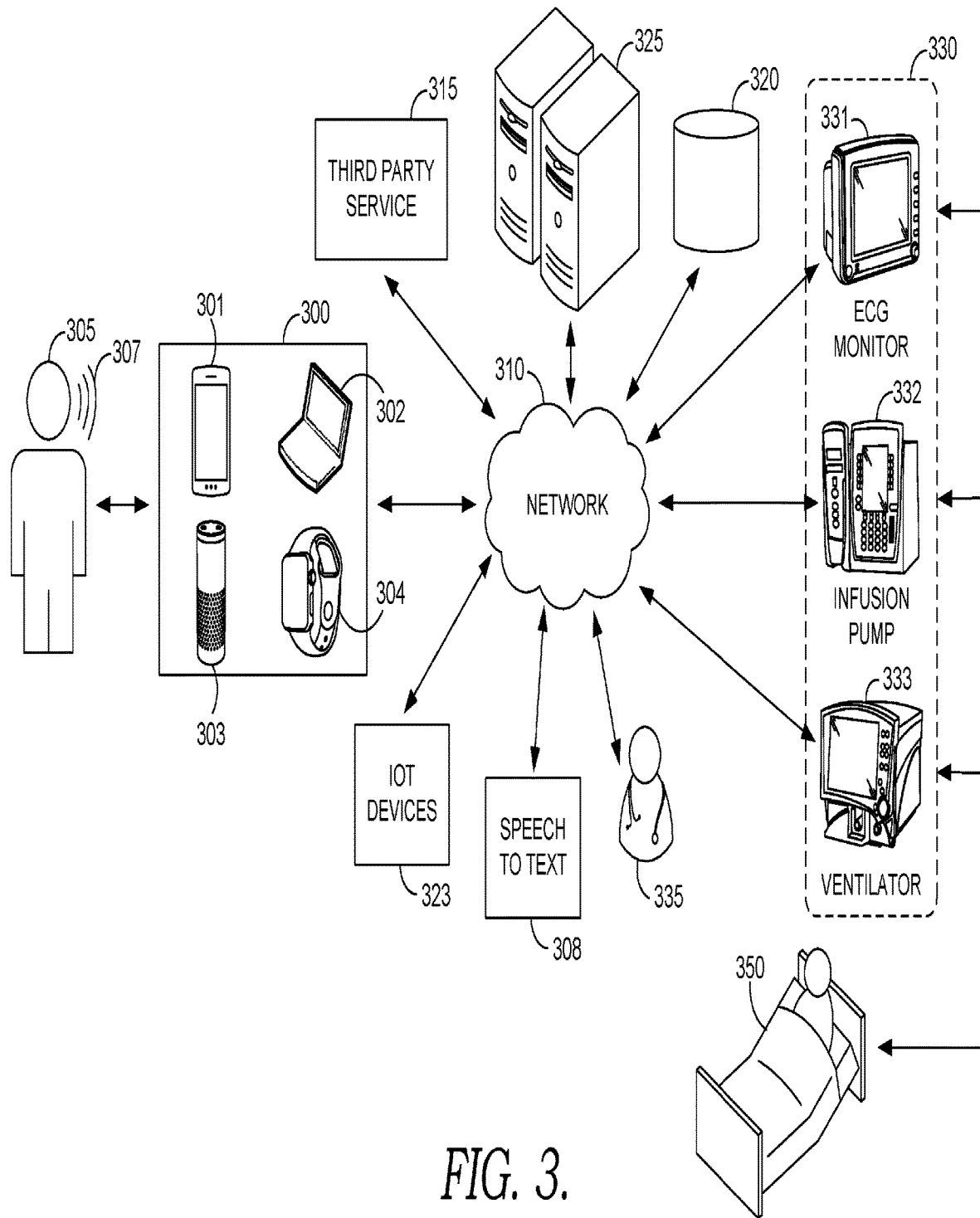
FIG. 3 is an block diagram of an exemplary integrated voice command system in accordance with an aspects herein.

Turning now to FIG. 3, FIG. 3 illustrates another exemplary system for integrating medical devices with voice control. Here, a user 305 may make a request in the form of an audible signal 307 that is received by the listening device 300. The listening device 300 may comprise any number of devices. Some examples are a cellular phone 301, a notebook computer 302, a stationary personal assistant 303, a smartwatch 304, and the like. The listening device 300 may be communicatively coupled to a network 310.

The network 310 may be integrated with datastore 320, which may be an electronic medical record system. The network 310 may be further integrated with a third-party service 315, a control component 325, and any number of medical devices 330, such as an ECG 331, an infusion pump 332, a ventilator 333, and the like. One or more medical devices 330 may be associated with patient 350. Therefore, for example, the medical devices 330 may be integrated with the electronic medical record system, the control component 325, and the third-party service 315 through the network 310. In some cases, Internet of Things (IoT) devices 323 and technology may additionally be integrated with the network 310 and controlled by control component 325. For example, lights, thermostats, televisions, and the like may all be controlled via the control component 325.

Thus, for example, the listening component 300 may receive the audible signal 307 request. In some cases, the request may be to generate an order to be stored in a patient's 350 medical records or to adjust a medical device 330 associated with the patient 350. The network 310 may receive the voice request from the listening device 300. The voice request may be translated by into text and/or into computer readable code via a speech-to-text component 308 that is in communication with network 310. The control component 325, coupled to the network 310, may determine the response based on the translated request. For instance, if the request is to generate an order for the patient 350, the control component 325 may verify the identity of the requesting party and confirm that the requesting party is authorized to make the request. The control component 325 may then generate an order based on the request and store the order in the electronic medical record system in association with the patient 350. The order may then be accessed by people and devices in communication with the network 310. For example, one of the medical devices 330 may perform an action on the patient 350 in accordance with the order. In another scenario, the request may be to adjust one of the medical devices 330 associated with the patient. The control component may receive the translated request and send to the medical device 330, via the network 310, device-specific instructions to perform an adjustment in accordance with the instructions.

In some aspects, the network 310 may be integrated with or in communication with other users 335 of the system via communication devices. Thus, a voice command can be given to the listening device 300 to send a message to another user 335. The speech-to-text component 308 may translate the message into human readable text that is sent to the communication device of the other user 335 via the control component 325. In this same fashion, the control component 325 may make appointments for the patient 350 with other users 335, such as other clinicians. In some cases, other users 335 may receive requests to follow-up with the patient 350, such as a consult. In some aspects, alerts or notifications may be sent to multiple users, such as user 335, of the system, via the control component through network 310. For example, if one of the medical devices 330 associated with the patient 350 detects that a variable being monitored is outside the threshold amount, the device may send notifications or alerts to user 335.

Figure 4:
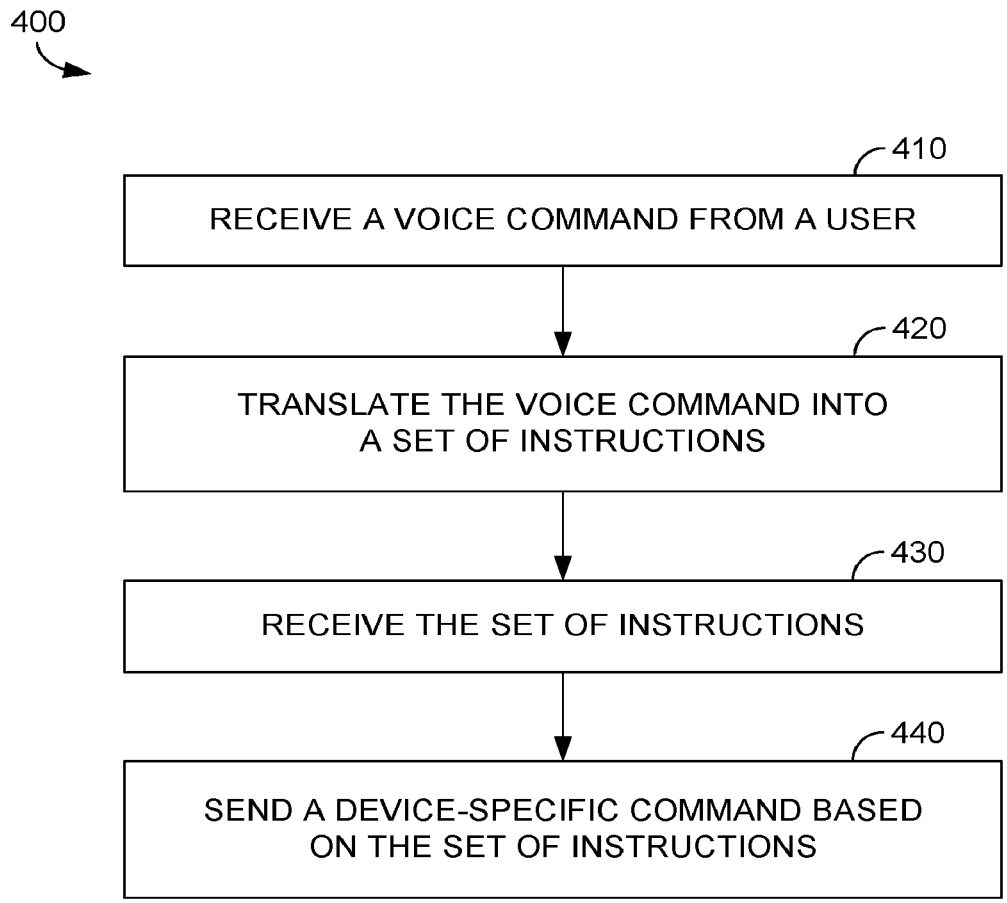
FIG. 4 is a block diagram of an exemplary method that may be performed by aspects described herein.

FIG. 4 illustrates a block diagram of an exemplary method 400 that may be performed by aspects described herein. At step 410, the method comprises receiving a voice command. For example, the voice command may be received at a listening component having a microphone. At step 420, the method comprises translating the voice command into usable instructions. For example, this may be done through a speech-to-text technology or service, and may be translated into human readable or machine readable format. And at step 430, the method comprises providing the instructions to a medical device or system associated with the patient. For example, this could be provided to a device so that the device takes an action on the patient, or may be provided to the medical records system to store the request in association with the patient.

FIGS. 5A-5C present a computer-readable code for implementing an exemplary use scenario. It should be noted that the code in FIGS. 5A-5C is one of many ways to implement the present technology, and it only presents an exemplary scenario. Particularly, the code as illustrated in FIGS. 5A-5C presents one way that a user may adjust an alarm limit on a monitor that is actively monitoring a patient.

From the foregoing, it will be seen that this technology is one well adapted to attain all the ends and objects described, and together with other advantages which are obvious and inherent to the structure. It will be understood that certain features and subcombinations are of utility and may be employed without reference to other features and subcombinations. This is contemplated by and is within the scope of the claims. Since many possible embodiments may be made of the present technology without departing from the scope, it is to be understood that all matter described or shown in the accompanying drawings is to be interpreted as illustrative and not in a limiting sense.

What is claimed is:

1. A method comprising:
receiving an audio signal corresponding to a sound made by a user;
converting the audio signal into a set of instructions including an instruction for administering a medical treatment to a patient using a particular medical device;
determining that the user is authorized to instruct the particular medical device to administer the medical treatment to the patient by comparing the user to a list of users authorized to instruct medical devices to administer medical treatments to the patient, the list of users stored in an electronic health record for the patient; wherein an electronic health information system stores the electronic health record for the patient and a plurality of other electronic health records for a plurality of other patients;
determining that the medical treatment corresponds to a prescribed medical treatment for the patient included in the electronic health record for the patient; and
in response to the determining that the user is authorized and that the medical treatment corresponds to the prescribed medical treatment, automatically instructing the particular medical device to administer the medical treatment to the patient according to the instruction; and
in response to automatically instructing the particular medical device to administer the medical treatment to the patient according to the instruction, updating the electronic health record for the patient with an indication that the medical treatment has been administered to the patient.

2. The method of claim 1, wherein the audio signal includes a voice command for the particular medical device.

3. The method of claim 1, wherein the audio signal is received by a listening device communicatively coupled to the particular medical device.

4. The method of claim 1, wherein the audio signal is received by a listening device integrated into the particular medical device.

5. The method of claim 1, wherein comparing the user to the list of users authorized to instruct medical devices to administer medical treatments to the patient comprises verifying an identity of the user.

6. The method of claim 1, wherein the prescribed medical treatment corresponds to an amount of medication to be administered.

7. The method of claim 1, wherein automatically instructing the particular medical device to administer the medical treatment to the patient according to the instruction comprises adjusting one or more settings of the particular medical device.

8. A system comprising:
a processing system; and
one or more computer readable storage media storing instructions which, when executed by the processing system, cause the system to perform a method comprising:
receiving an audio signal corresponding to a sound made by a user;
converting the audio signal into a set of instructions including an instruction for administering a medical treatment to a patient using a particular medical device;
determining that the user is authorized to instruct the particular medical device to administer the medical treatment to the patient by comparing the user to a list of users authorized to instruct medical devices to administer medical treatments to the patient, the list of users stored in an electronic health record for the patient; wherein an electronic health information system stores the electronic health record for the patient and a plurality of other electronic health records for a plurality of other patients;
determining that the medical treatment corresponds to a prescribed medical treatment for the patient included in the electronic health record for the patient; and
in response to the determining that the user is authorized and that the medical treatment corresponds to the prescribed medical treatment, automatically instructing the particular medical device to administer the medical treatment to the patient according to the instruction; and in response to automatically instructing the particular medical device to administer the medical treatment to the patient according to the instruction, updating the electronic health record for the patient with an indication that the medical treatment has been administered to the patient.

9. The system of claim 8, wherein the audio signal includes a voice command for the particular medical device.

10. The system of claim 8, wherein the audio signal is received by a listening device communicatively coupled to the particular medical device.

11. The system of claim 8, wherein the audio signal is received by a listening device integrated into the particular medical device.

12. The system of claim 8, wherein comparing the user to the list of users authorized to instruct medical devices to administer medical treatments to the patient comprises verifying an identity of the user.

13. The system of claim 8, wherein the prescribed medical treatment corresponds to an amount of medication to be administered.

14. The system of claim 8, wherein automatically instructing the particular medical device to administer the medical treatment to the patient according to the instruction comprises adjusting one or more settings of the particular medical device.

15. One or more non-transitory computer-readable media storing computer-readable instructions that, when executed by a processing system, cause a system to perform a method comprising:

receiving an audio signal corresponding to a sound made by a user;

converting the audio signal into a set of instructions including an instruction for administering a medical treatment to a patient using a particular medical device;

determining that the user is authorized to instruct the particular medical device to administer the medical treatment to the patient by comparing the user to a list of users authorized to instruct medical devices to administer medical treatments to the patient, the list of users stored in an electronic health record for the patient; wherein an electronic health information system stores the electronic health record for the patient and a plurality of other electronic health records for a plurality of other patients;

determining that the medical treatment corresponds to a prescribed medical treatment for the patient included in the electronic health record for the patient; and in response to the determining that the user is authorized and that the medical treatment corresponds to the prescribed medical treatment, automatically instructing the particular medical device to administer the medical treatment to the patient according to the instruction; and in response to automatically instructing the particular medical device to administer the medical treatment to the patient according to the instruction, updating the electronic health record for the patient with an indication that the medical treatment has been administered to the patient.

16. The one or more non-transitory computer-readable media of claim 15, wherein the audio signal includes a voice command for the particular medical device.

17. The one or more non-transitory computer-readable media of claim 15, wherein the audio signal is received by a listening component of an electronic device.

18. The one or more non-transitory computer-readable media of claim 15, wherein comparing the user to the list of users authorized to instruct medical devices to administer medical treatments to the patient comprises verifying an identity of the user.

19. The one or more non-transitory computer-readable media of claim 15, wherein the prescribed medical treatment corresponds to an amount of medication to be administered.

20. The one or more non-transitory computer-readable media of claim 15, wherein automatically instructing the particular medical device to administer the medical treatment to the patient according to the instruction comprises adjusting one or more settings of the particular medical device.

* * * * *